United States Patent [19]
Proud et al.

[11] Patent Number: 4,576,185
[45] Date of Patent: Mar. 18, 1986

[54] COLLECTION DEVICE FOR CAPILLARY BLOOD

[75] Inventors: Todd A. Proud, Claymont; Tom F. Lin, Bear, both of Del.; Wayne J. Mitchell, Elkton, Md.; James D. Kasper, Montpelier, Ohio

[73] Assignee: Terumo Medical Corporation, Elkton, Md.

[21] Appl. No.: 557,962

[22] Filed: Dec. 5, 1983

[51] Int. Cl.⁴ .............................................. A61B 5/14
[52] U.S. Cl. .................................... 128/760; 604/189; 604/192; 220/356
[58] Field of Search ............... 128/760, 762, 763, 765, 128/770, 764, 766, 771, 643; 604/189, 192, 197–198; 220/356

[56] References Cited

U.S. PATENT DOCUMENTS

| 3,381,872 | 5/1968 | Holder et al. | 220/356 X |
| 3,518,164 | 6/1970 | Andelin et al. | 128/760 X |
| 3,623,475 | 11/1971 | Sanz et al. | 128/762 |
| 3,640,267 | 2/1972 | Hurtig et al. | 128/765 |
| 3,750,645 | 8/1973 | Bennett et al. | 128/760 |
| 3,809,068 | 5/1974 | Kosowsky | 128/765 |
| 3,898,982 | 8/1975 | Katsuda | 128/760 |
| 3,902,477 | 9/1975 | Gerarde | 128/760 |
| 3,926,521 | 12/1975 | Ginzel | 356/39 |
| 3,957,653 | 5/1976 | Blecher | 210/518 |
| 4,024,857 | 5/1977 | Blecher et al. | 128/763 |
| 4,069,185 | 1/1978 | Sullivan | 523/112 |
| 4,087,567 | 5/1978 | Sullivan | 427/2 |
| 4,112,925 | 9/1978 | Sullivan | 128/760 |
| 4,132,225 | 1/1979 | Whattam | 128/763 |
| 4,152,939 | 5/1979 | Renshaw | 73/864.02 |
| 4,210,156 | 7/1980 | Bennett | 128/763 X |
| 4,215,700 | 8/1980 | Crouther et al. | 128/763 |
| 4,227,620 | 10/1980 | Conway | 128/763 X |
| 4,250,893 | 2/1981 | White | 128/765 |
| 4,304,241 | 12/1981 | Brennan | 128/743 |
| 4,360,016 | 11/1982 | Sarrine | 128/763 |
| 4,397,318 | 8/1983 | Burns | 128/763 |
| 4,411,163 | 10/1983 | White | 73/864.02 |

FOREIGN PATENT DOCUMENTS

| 72006 | 2/1983 | European Pat. Off. |
| 3201691 | 9/1983 | Fed. Rep. of Germany |
| 2173661 | 10/1973 | France |
| 606415 | 8/1983 | Japan |

OTHER PUBLICATIONS

Patents Abstracts of Japan, vol. 6, No. 237, 11/25/72.
Becton Dickinson and Company; Inside; The New Flotop Collector; 1981.
Monoject Samplette Capillary Blood Separator.

Primary Examiner—Kyle L. Howell
Assistant Examiner—Angela D. Sykes
Attorney, Agent, or Firm—Connolly and Hutz

[57] ABSTRACT

A collection device for capillary blood includes a collector having an upper end for placement in the close proximity to the punctured skin so that the blood will be conveyed into an integral tubular container. A removable closure is provided at the top of the collector to seal the collector during non-collecting use. The closure is structured so that the container may nest therein while blood is being collected.

8 Claims, 18 Drawing Figures

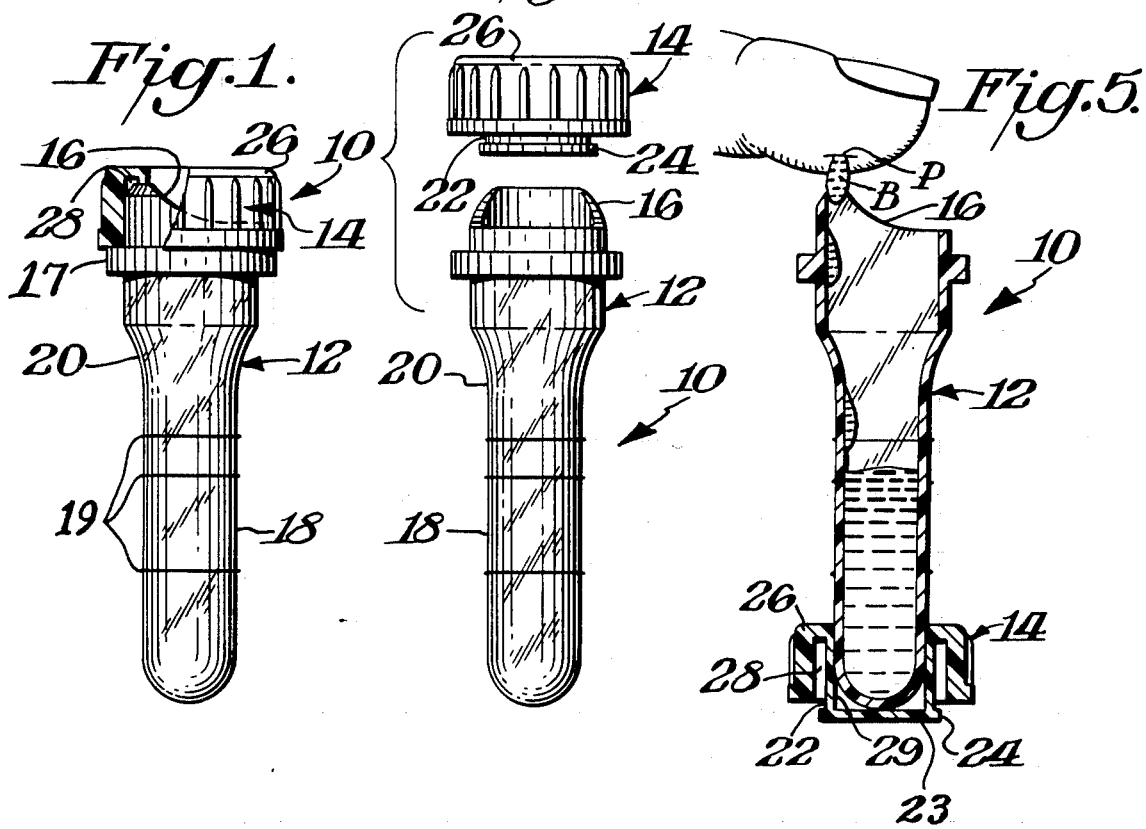

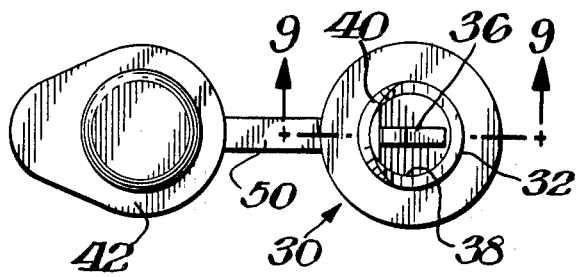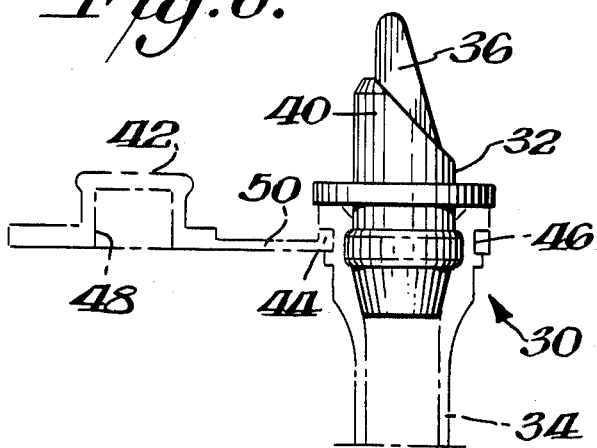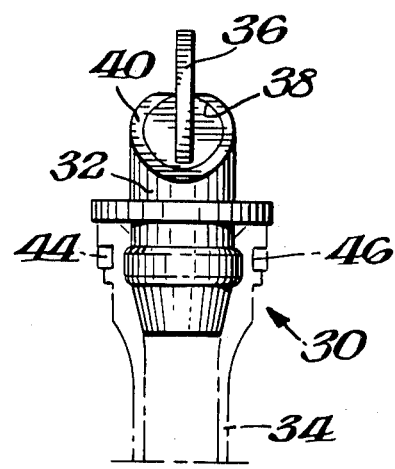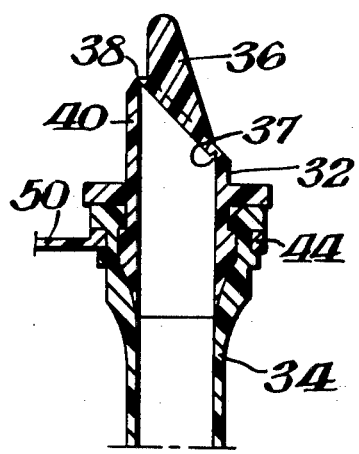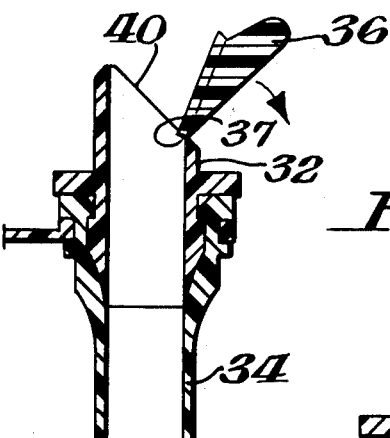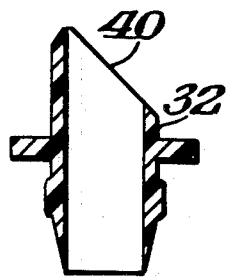

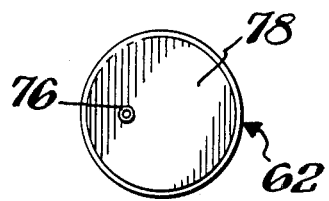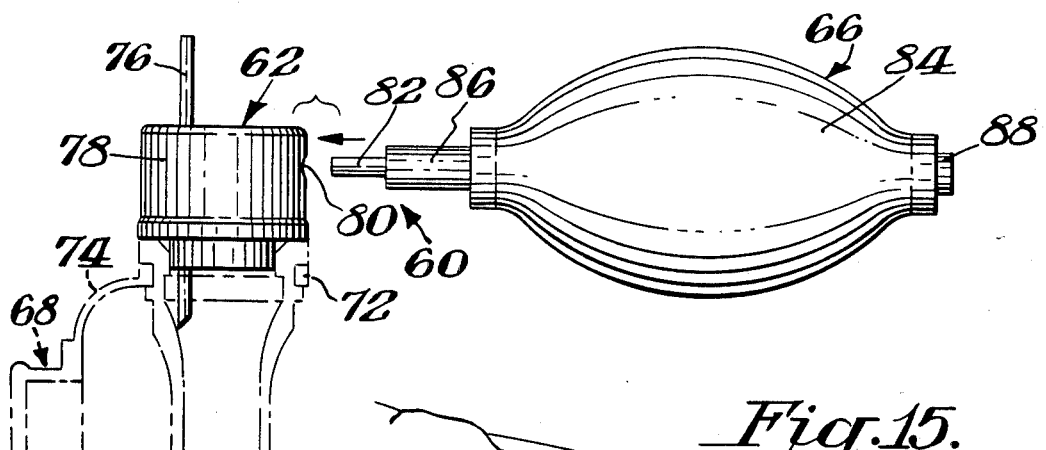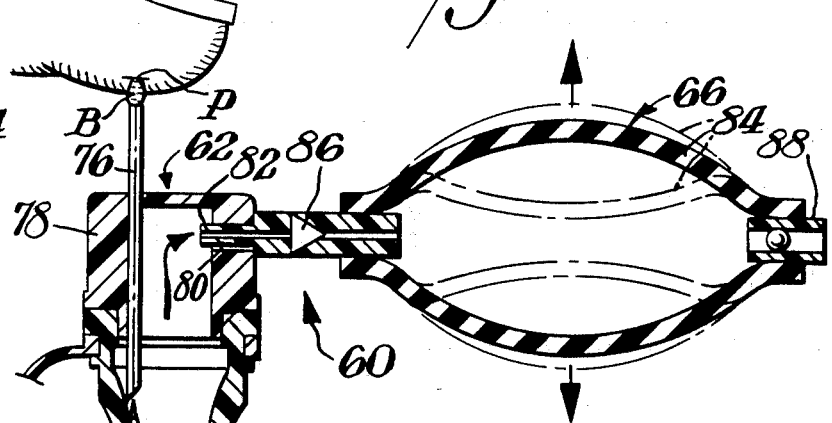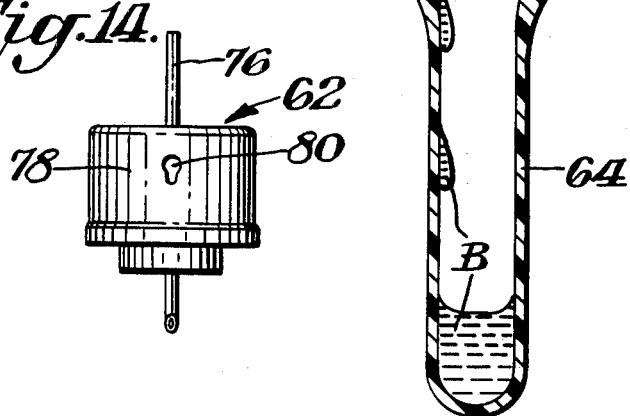

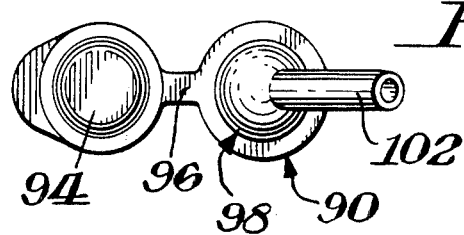
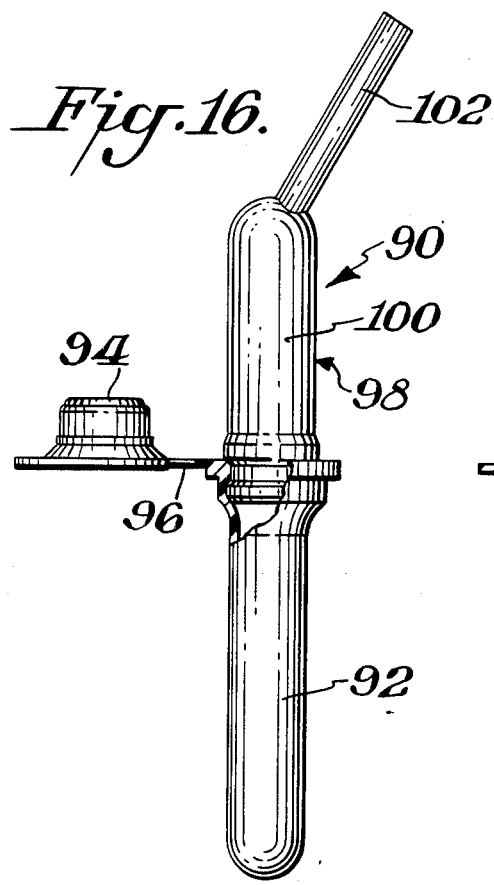
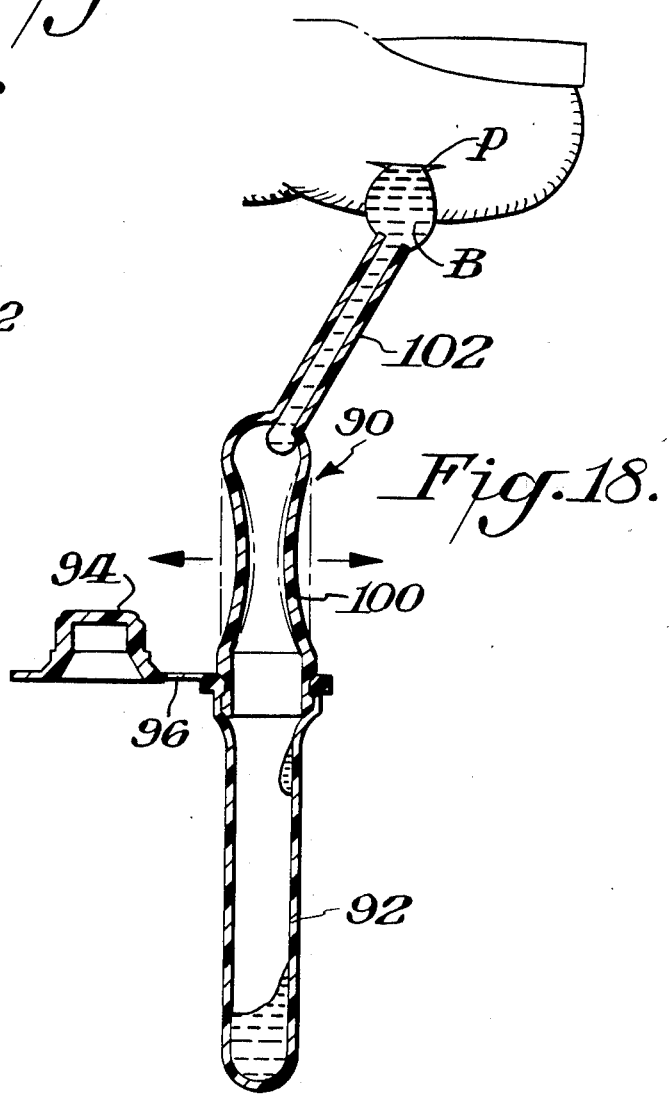

4,576,185

COLLECTION DEVICE FOR CAPILLARY BLOOD

BACKGROUND OF THE INVENTION

Various forms of collection devices for capillary blood presently exist. For the most part such devices are unsatisfactory for a number of reasons. For example, the interior of the containers are generally exposed to atmospheric conditions as packaged and/or there is a need for assembly of separate parts before and after blood collection. Such presently existing devices also are of such a design that the chance of the specimen clotting during sample collection is quite great. Additionally such devices are inefficient in blood sampling.

SUMMARY OF THE INVENTION

An object of this invention is to provide a collection device for capillary blood which comprises a pre-assembled ready to use closed system.

A further object of this invention is to provide such a device which includes means to readily identify the type of additive therein.

It is a further object of this invention to provide such a device which is characterized by ease of operation and handling while minimizing the chance of specimen clotting during collection.

In accordance with a preferred form of this invention the collection device for capillary blood comprises an integral blood collector-container which functions both to collect and to contain capillary blood during skin puncture. The device preferably also includes a separate color coded closure which is used to seal the collector-container before and after sample collection. Additionally the closure is designed in such a manner that the bottom of the collector-container can be nested into the top of the closure during sample collection.

In accordance with a further form of this invention a tear tab seals the collector during storage and shipping. After disposal of the tear tab, the collector acts to convey blood from the puncture site to the tubular container and a separate closure would function to seal the container.

In an alternative form of this invention means are provided to facilitate the flow of blood into the container by aiding the force of gravity with pump suction or aspirating means.

THE DRAWINGS

FIG. 1 is a side elevation view partly in section of a collection device for capillary blood in accordance with this invention;

FIG. 2 is a top plan view of the device shown in FIG. 1;

FIG. 3 is a front elevation exploded view showing the collector-container and closure of the device of FIGS. 1–2;

FIG. 4 is a top plan view of the device of FIGS. 1–3 with the collector-container nested into the closure;

FIG. 5 is a cross-sectional view taken through FIG. 4 along the line 5—5 and showing the device during sample collection;

FIG. 6 is a side elevation view of a modified form of this invention with the tube and closure shown in phantom;

FIG. 7 is a top plan view of the device shown in FIG. 6;

FIG. 8 is a front elevation view of the device shown in FIGS. 6–7;

FIG. 9 is a cross-sectional view taken through FIG. 7 along the line 9—9;

FIGS. 10–11 are views similar to FIG. 9 in different phases of operation;

FIG. 12 is an exploded view of yet another form of this invention with the closure and tube indicated in phantom.

FIG. 13 is a top plan view of the capillary unit shown in FIG. 12;

FIG. 14 is a front elevation view of the capillary unit shown in FIGS. 12–13;

FIG. 15 is a cross-sectional view in elevation of the device shown in FIGS. 12–14 during the sampling phase of operation;

FIG. 16 is a front elevation view partly in section of yet another embodiment of this invention;

FIG. 17 is a top plan view of the device shown in FIG. 16; and

FIG. 18 is a cross-sectional view in elevation of the device shown in FIGS. 16–17 during the sampling phase of operation.

DETAILED DESCRIPTION

FIGS. 1–4 show collection device for capillary blood 10 in accordance with this invention. As illustrated therein, the device 10 includes two components, namely an integral blood collector-container 12 and a closure 14. Collector-container 12 is preferably a one piece disposable plastic part. The collector portion or top 16 has an outwardly extending arcuate lip at a portion of its periphery and functions to act as a collector of capillary blood to convey the blood B effectively from the skin puncture site P to the container portion 18 as shown in FIG. 5. The bottom of container portion 18 is generally tubular in shape with the lowermost end being rounded or dome shaped. Container portion 18 is thus formed similar to a centrifuge tube having a closed bottom and tapered upper end 20. Tube 18 can be filled with blood to any desired level. If desired, an additive such as blood anticoagulant, clot activator and/or gel material, etc. may be precoated or added to container 18 prior to blood collection. Advantageously the collector-container 12 can then be used as a tube for centrifuging during specimen preparation.

In accordance with this invention closure 14 is color coded. In this respect a different colored closure could be provided with each collector-container corresponding to the type of additive in that container. Thus the user would readily know what type of additive has been provided by a quick visual inspection of the particular closure with regard to the color thereof. Preferably closure 14 is made of a moldable material consisting of a round plug 22 extending axially downwardly so as to fit snugly in the collector portion 16 of the device as shown in FIGS. 1 and 3. In this manner of use plug 22 which is provided with a resilient annular flange 24 functions as an effective seal over the open end of the collector-container 12. As best shown in FIGS. 3 and 5, plug 22 extends from an overcap or main body member 26 with an annular channel 28 formed between the outer surface of plug 22 and the inner surface of overcap 26. When closure 14 functions as a seal, collector portion 16 fits snugly in channel 28 and overcap 26 forms an effective collector shield. Thus the interior of collector-container 12 is sealed by flange 24 while the exterior of collector 16 is shielded by overcap 26. The result is an effective seal for the collector-container 12 during shipping and storage to insure the integrity of the additive in the container before sample collection.

During blood collection the closure 14 is removed and the bottom of tube 18 is nested in the hollow interior 29 of plug 22 as shown in FIG. 5.

Closure 14 functions not only as a seal prior to blood collection but has additional functions. One such function is that after the sample has been collected and the closure 14 is inserted into collector container 12, the plug 22 acts as a wipe to sweep any blood that may be in the collector portion 16 into the tube portion 18. Additionally closure 14 continues to function as a seal after sample collection. As shown in FIG. 1, collector portion 16 includes a flange 17 which acts as a stop for limiting the amunt of downward movement of closure 14 whereby the upper edge or lip of collector portion 16 is spaced from the wall bridging overcap 26 and plug 22. FIGS. 1, 3 and 5 also illustrate circumferential lines 19 arund tube 18 which would indicate different volume levels of tube 18. FIG. 5 also illustrates plug 22 terminating in a flat lower wall 3 which extends between overcap 26. As showni n FIG. 5, the rounded end of tube 18 fits within plug 22 in contact with wall 23.

The operation of device 10 would be as follows. Device 10 would be in the pre-assembled form shown in FIG. 1. Closure 14 would be removed and the bottom of collector-container 12 would nest in the top of closure 14 as shown in FIG. 5. The skin of the patient would be punctured and the lip portion of the collector 16 would act to convey capillary blood B into collector 16 while the device 10 is held in a vertical position. The blood B would flow by gravity through collector portion 16 and into container portion 18 until a sufficient sample has been obtained. Closure 14 would then be removed from the bottom of container 18 and inserted into collector 16 to again effectively seal the device. The contents of the collector could then be mixed with the additives by gentle inversion such as eight to ten times and the specimen would be in a condition to be sent to a laboratory for testing.

Device 10 is particularly advantageous in that it provides a pre-assembled ready to use closed system collection device for capillary blood. The parts of device 10 can readily be molded by conventional methods employing moldable materials such as plastic and/or rubber which are inert to blood reagents.

FIGS. 6–11 show a modified form of this invention with respect to the means for sealing the device. As indicated therein, device 30 includes a disposable collector 32 which is detachably secured to a container 34. Any suitable means may be used for securing collector 32 to container 34 such as by snapping the parts together through use of the inherent resiliency in the materials used for making the parts. Device 30 includes a tear tab closure 36 which is secured by means of a thin membrane 38 to the open top of collector 32. During initial assembly and until device 30 is used for actually collecting a blood sample, collector 32 and its tear tab 36 thereby function as a closure for container 34.

As with the prior embodiment, collector 32 has a scoop-like shape at its top 40 which may be placed at the puncture site for collecting the blood and directing it into container 34. As with the prior embodiment, container 34 might also include a suitable additive. Thus the combined closure collector assures the integrity of the additive during shipping and storage. When the device 30 is to act as a collector and container, tab 36 would be pulled downwardly as shown in FIG. 10 to tear the ultra-thin membrane 38 at its weakened connection 37 so that the entire tab 36 may then be removed leaving collector 32 in the condition shown in FIG. 11 while in this condition, collector 32 performs its second function of conveying the blood effectively into container 34.

Container 34 would be of tubular form much the same as container 18 illustrated, for example, in FIG. 5. Container 34 is preferably of a molded plastic similar to a centrifuge tube which includes a closed bottom and tapered upper end. This tapered upper end has an inner configuration which is shaped to complement the outer configuration of collector 32 to thereby result in a tightly fitted connection of collector 32 and container 34.

Closure 42 would be made of any suitable material and is preferably molded with a ring 44 at one end for attachment to container 34 by being snapped into an annular groove 46. Ring 44 would be connected to cap portion 48 of closure 42 in any suitable manner such as by a flexible strap 50. Ring 44 would be conveniently snapped into groove 46 by sliding the ring up from the bottom of tubular container 34 and then into groove 46. As previously described, closure 42 could be color coded to indicate the type of additive in container 34.

After a sufficient sample has been collected, collector 32 would be removed from container 34 and container 34 would be sealed by closure 42 so that the specimen could then be sent, for example, to a laboratory for testing.

FIGS. 12–15 show yet another device 60 in accordance with this invention. Device 60 includes a disposable capillary unit collector 62 which may be made of any suitable material such as a plastic material and which functions as an effective blood conveyor from the blood source or puncture site P (FIG. 15) to the container portion 64 when incorporated with a suction unit 66. Suction unit 66 may be disposable or reuseable and may be of any suitable form so as to be adaptable for operation with capillary unit 62. Suction unit 66 functions as a suction pump to accelerate blood flow through the capillary unit 62. By attaching suction unit 66 to capillary unit 62, blood is conveyed by a combination of forces, namely, gravity, capillary action and pump suction. The combination of conveying forces provides distinct superiority to conventional capillary blood collection devices relying solely on gravity. Container 64 would be of generally the same construction as container 34 and thus would include a color coded closure 68 in the form of a cap 70 attached to a ring 72 by means of a flexible strap 74. Ring 72 is engaged in a groove in the neck of container 64.

Capillary unit 62 consists of a capillary tube 76 which runs through a plastic body 78. As shown in FIG. 15, body 78 is provided with an open bottom and a sealed top. The thickened side wall of body 78 may have a specially shaped passage such as a keyhole opening 80. The opening 80 provides a vent for the system to facilitate the flow of blood by capillary action and serves as an opening for attachment of the stem portion 82 of the suction unit 66 so that when the suction unit 66 is activated, the blood flow during sampling is accelerated.

Suction unit 66 consists of a flexible bulb 84 which is provided with a oneway inlet checkvalve 86 and a oneway outlet checkvalve 88. The function of suction unit 66 is to create suction by repetitive squeezing. It is to be understood that for simplicity, the suction unit may consist of a flexible bulb alone or with any combination of checkvalves and/or vents.

As previously indicated, container 64 is of similar construction to container 34. Its open upper end would be tight fitted to the aspirator system so that upon squeezing the flexible bulb 84, an effective suction would be created at the tip of the capillary during blood sampling. Bulb 84 would be so selected that its capacity would be large enough that upon releasing tension of the bulb, the suction created would overcome the suction lost at the vent.

After a sufficient sample has been collected, capillary unit 62 and suction unit 66 would be removed from container 64. Closure 68 would then seal the top of container 64. Prior to collection of the sample, capillary unit 62 and container 64 would be pre-assembled. Immediately prior to use, the stem 82 of inlet valve 86 would be inserted into opening 80 at the side of capillary unit 62. The patient's skin would then be punctured and capillary tube 76 would be disposed at the puncture site as indicated in FIG. 15 after bulb 84 had been squeezed to expel air. Bulb 84 would then be repetitively squeezed until container 64 is filled with blood to the desired level.

FIGS. 16–18 show an alternative form of providing a suction force to aid gravity in collecting a blood sample. The device 90 of FIGS. 16–18 includes a container 92 provided with a closure 94 which may be integrally attached by means of a connecting strap 96. Removably inserted in the open upper end of container 92 is an aspirator collector 98 in the form of a flexible body 100 having an integral capillary tube 102.

In use, aspirator 98 would be mounted to container 92. The skin would be punctured as shown in FIG. 18 and the preassembled device 90 would be held in a vertical position with tube 102 at the puncture site P. Body 100 would be squeezed to expel air preferably before the tube 102 is disposed at the puncture site P. Body 100 would be repetitively squeezed to aspirate blood through tube 102 until the desired amount is obtained in container 92. Aspirator 98 would then be removed from container 92 and closure 94 would be inserted to the top of container 92 to seal the container.

It is to be understood that for the sake of simplicity in describing various aspects of this invention, four different devices have been illustrated. Such separate illustration of devices, however, is not intended to limit the invention in that, where appropriate features of one device may be incorporated in other devices. For example, each of the devices may use a color coded closure. Similarly each of the closures may be detachably secured to the container, and during collecting use of the device, the container may nest in the closure. Similarly each of the devices may include a tear tab as an initial sealing means. Additionally, various forms of aspirators as illustrated by devices 60 and 90 may be included in combination with other devices such as devices 10 and 30.

What is claimed is:

1. A collection device for capillary blood comprising a container portion in the form of a tube having an open uper end and a closed lower end, a collector portion secured to said upper end of said tube in flow communication therewith, said collector portion having upper and lower ends, inner and outer surfaces, and further including means for conveying blood from a user and into said container portion, closure means for selectively sealing the upper end of said collector portion during non-collecting use of said device, said closure means having a recess of a shape and dimension whereby said lower end of said tube is selectively nested into said closure recess during collecting use of said device, said collector portion being integral with said container portion, said upper end of said collector portion being in the form of an arcuate lip extending coaxially therefrom to comprise said blood conveying means, said closure means including an overcap, an axial plug extending downwardly away from said overcap with an annular channel therebetween formed by a wall bridging said overcap and said axial plug, a resilient annular flange extending radially outwardly from said axial plug, said resilient annular flange being dimensioned to snugly slide in said collector portion, said resilient annular flange comprising wipe means for wiping the inner surface of said collector portion when said closure means is applied thereto, said plug sealing said collector portion, said lip fitting in said annular channel whereby said overcap comprises a shield for said collector portion during non-collecting use of said device, stop means on the outer surface of said collector portion located to limit the downward movement of said overcap to maintain said lip spaced from said wall bridging said overcap and said plug, and said plug being hollow with an open upper end to comprise said recess.

2. The device of claim 1 wherein said tube includes an additive, and said closure means being color coded to provide a visual identification of said additive.

3. The set of claim 1 wherein said stop means comprises an annular flange around the outer surface of said collector portion, and volume indicating lines being on said container portion.

4. The device of claim 1 wherein said lower end of said container portion is rounded, and said axial plug terminating in a flat lower wall which is located beyond said overcap.

5. A set of collection devices for capillary blood, each of said devices comprising a container portion in the form of a tube having an open uper end and a closed lower end, a tubular collector portion integral with said upper end of said container portion in flow communication therewith, said collector portion having inner and outer surfaces, said container portion being of lesser diameter than the diameter of said collector portion and being joined thereto by a tapered tubular section, the upper end of said collector portion terminating in an arcuate lip extending co-axially outwardly from a part of said upper end of said collector portion with the remaining part of said upper end being of a lesser length than the length of said arcuate lip, said arcuate lip comprising blood conveying means for directing blood into said collector portion, closure means for selectively sealing said upper end of said collector portion during non-collecting use of said device, said closure means including an overcap in the form of a hollow tube, an axial plug extending downwardly away from and coaxially within said overcap with an annular channel therebetween formed by a wall bridging said overcap and said axial plug, a resilient annular flange extending radially outwardly from said axial plug said resilient annular flange being dimensioned to snugly slide in said collector portion, said resilient annular flange comprising wipe means for wiping the inner suface of said collector portion when said closure means is applied thereto, said plug sealing said collector portion, said arcuate lip fitting in said annular channel whereby said overcap comprises a shield for said collector portion during non-collecting use of said device, said plug being hollow with an open upper end which comprises an exposed tubular recess, said tubular recess being of a diameter with respect to said container portion to permit said container portion to snugly nest in said recess during the collecting use of said device, an additive being included in said device, and each of said closure means being color coded in accordance with the particular additive in its device of said set whereby each closure means provides a readily visual indication of the particular additive included in its device.

6. The set of claim 5 including stop means on the outer surfaces of said collector portion on each of said devices, said stop means being located to limit the downward movement of said overcap to maintain said lip spaced from said wall bridging said overcap and said plug.

7. The set of claim 6 wherein said stop means comprises an annular flange around the outer surface of said collector portion, and volume indicating lines being on said container portion.

8. The set of claim 15 wherein said lower end of each container portion is rounded, and said axial plug terminating in a flat lower wall which is located beyond said overcap.

* * * * *